US011681984B2

(12) United States Patent
Kimmel et al.

(10) Patent No.: US 11,681,984 B2
(45) Date of Patent: Jun. 20, 2023

(54) INVENTORY MANAGEMENT SYSTEMS AND RELATED METHODS

(71) Applicant: Scaled Solutions Technologies LLC, San Marcos, CA (US)

(72) Inventors: Kyle L. Kimmel, San Diego, CA (US); Jeffrey D. Anson, San Diego, CA (US); Thomas M. Lugo, III, San Diego, CA (US); Joshua Paul Smith, San Diego, CA (US)

(73) Assignee: Scaled Solutions Technologies LLC, San Marcos, CA (US)

( * ) Notice: Subject to any disclaimer, the term of this patent is extended or adjusted under 35 U.S.C. 154(b) by 184 days.

(21) Appl. No.: 16/998,940

(22) Filed: Aug. 20, 2020

(65) Prior Publication Data

US 2022/0058577 A1    Feb. 24, 2022

(51) Int. Cl.
| | | |
|---|---|---|
| *G06Q 10/08* | (2023.01) | |
| *G16H 10/40* | (2018.01) | |
| *G16H 40/20* | (2018.01) | |
| *G06Q 10/10* | (2023.01) | |
| *G06K 7/10* | (2006.01) | |
| *G06K 7/14* | (2006.01) | |
| *G06N 20/00* | (2019.01) | |
| *G06Q 10/04* | (2023.01) | |
| *G06Q 10/0875* | (2023.01) | |

(52) U.S. Cl.
CPC ..... *G06Q 10/0875* (2013.01); *G06K 7/10366* (2013.01); *G06K 7/1413* (2013.01); *G06K 7/1417* (2013.01); *G06N 20/00* (2019.01); *G06Q 10/04* (2013.01); *G06Q 10/10* (2013.01); *G16H 10/40* (2018.01); *G16H 40/20* (2018.01)

(58) Field of Classification Search
CPC .... G06Q 10/0875; G06Q 10/10; G06Q 10/04; G16H 10/40; G16H 40/20; G06K 7/10366; G06K 7/1417; G06K 7/1413; G06N 20/00
USPC ..................................................... 705/20, 29
See application file for complete search history.

(56) References Cited

U.S. PATENT DOCUMENTS

| | | |
|---|---|---|
| 4,581,762 A | 4/1986 | Lapidus |
| 4,869,396 A | 9/1989 | Horino |
| 5,174,399 A | 12/1992 | Brauneis |
| 5,410,108 A | 4/1995 | Williams |
| 5,986,219 A | 11/1999 | Carroll |

(Continued)

FOREIGN PATENT DOCUMENTS

| | | | |
|---|---|---|---|
| CN | 109965560 A | * | 7/2019 |
| EP | 3511036 | | 7/2019 |

(Continued)

*Primary Examiner* — Ariel J Yu
*Assistant Examiner* — Denisse Y Ortiz Roman
(74) *Attorney, Agent, or Firm* — Fresh IP PLC; John R. Bednarz; Emily Do

(57) ABSTRACT

Disclosed is an inventory management system capable of tracking and accounting for partially used inventory. The management system for partial inventory contains a scale scanner hardware component and a software database component. The system may also populate input tables for experiments or generate findings based on analyzed managed inventory. Further, the system may create reports based on the findings, which may contain supply and demand forecasts or inventory optimization recommendations.

20 Claims, 8 Drawing Sheets

(56) References Cited

U.S. PATENT DOCUMENTS

| | | |
|---|---|---|
| 6,092,726 A | 7/2000 | Toussant |
| 6,098,029 A | 8/2000 | Takagi |
| 6,450,406 B2 | 9/2002 | Brown |
| 6,601,764 B1 | 8/2003 | Goodwin |
| 7,458,260 B2 | 12/2008 | Roesner |
| 7,499,581 B2 | 3/2009 | Tribble |
| 7,813,973 B2 | 10/2010 | Gudbjartsson |
| 8,229,161 B2 | 7/2012 | Hudnut |
| 8,740,077 B2 | 6/2014 | Needham |
| 9,002,096 B2 | 4/2015 | Pronkine |
| 9,617,140 B2 | 4/2017 | Hershberger |
| 9,727,838 B2 | 8/2017 | Campbell |
| 10,055,851 B2 | 8/2018 | Spector |
| 10,332,066 B1 | 6/2019 | Palaniappan |
| 10,373,118 B1* | 8/2019 | Lefkow ............ G06Q 10/0875 |
| 10,837,974 B2* | 11/2020 | Postma ............ G06Q 30/0641 |
| 2005/0000737 A1 | 1/2005 | Fox |
| 2005/0197738 A1 | 9/2005 | Morrison |
| 2006/0178578 A1 | 8/2006 | Tribble |
| 2013/0159135 A1* | 6/2013 | Jones ................ G06Q 10/08 |
| | | 705/26.8 |
| 2014/0229343 A1* | 8/2014 | Higgins ............ G01G 23/3728 |
| | | 705/28 |
| 2015/0178654 A1* | 6/2015 | Glasgow ........... G06Q 10/0875 |
| | | 705/7.25 |
| 2016/0189489 A1* | 6/2016 | Au ..................... G06K 7/1413 |
| | | 235/383 |
| 2016/0264394 A1 | 9/2016 | Hershberger |
| 2017/0087555 A1 | 3/2017 | Morris |
| 2018/0303390 A1 | 10/2018 | Hatamian |
| 2019/0197466 A1 | 6/2019 | Hand |
| 2020/0074402 A1 | 3/2020 | Adato |

FOREIGN PATENT DOCUMENTS

| | | |
|---|---|---|
| JP | 2006138814 | 8/2010 |
| KR | 100593098 | 6/2006 |
| WO | 1999033008 | 7/1999 |
| WO | 2007006309 | 1/2007 |

\* cited by examiner

INVENTORY MANAGEMENT SYSTEMS AND RELATED METHODS

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO AN APPENDIX SUBMITTED ON A COMPACT DISC AND INCORPORATED BY REFERENCE OF THE MATERIAL ON THE COMPACT DISC

Not applicable.

STATEMENT REGARDING PRIOR DISCLOSURES BY THE INVENTOR OR A JOINT INVENTOR

Reserved for a later date, if necessary.

BACKGROUND OF THE INVENTION

Field of Invention

The disclosed subject matter is in the field of inventory management systems hardware and software.

Background of the Invention

Inventory management is a process which involves accounting for, controlling, monitoring, and/or maintaining the supply of an input product. At the most basic level, inventory management involves simply maintaining enough input substance or product supply for an organization to operate. Good inventory management leads to an organization running at a steady production pace, satisfying customers and achieving organizational deadlines. Poor inventory management, however, may lead to organizational, financial, and time inefficiencies. These inefficiencies may eventually lead to the failure of the entire organization.

Inventory management is a major organizational consideration because it is connected to supply chain management, production, finances, and customer outcomes. Supply chain management is tasked in part with is maintaining an adequate supply of inputs through purchasing. Adequate input supply is maintained by monitoring current input supply, forecasting input demand, and making orders based on the forecasts. A lapse or misjudgment in monitoring, forecasting, or purchasing may lead to an organization to have inadequate input supply. This may prove to be a substantial problem because having adequate input supply is essential to keeping production rates at optimum levels. Conversely, a lack of any essential inputs may put a temporary stop to production activities.

Organizations often make large investments into having adequate input supplies. Ideally, organizations buy in bulk because of reduced costs from suppliers and shipping. Further, having a large supply of inputs yields fewer production issues. However, all organizations have financial constraints and organizations often cannot afford to buy massive supplies of inputs at one time. Moreover, having a large supply of inputs may prove inefficient if demand for a related output decreases. Having a large supply of inputs may also be costly to warehouse. So, from a financial standpoint, it may be paramount to balance input supply purchasing with production, all while maintaining some amount of money on hand. In other situations, there may be financial incentives for organizations to have the minimum possible supply of inputs warehoused while maintaining a steady amount of is input orders. Undoubtedly, the best practices are nuanced, customized, and balanced in terms of organizational needs and financial constraints.

Customer satisfaction is also a major organizational consideration and it is often critical to the success or failure of the organization. Customers expect an output product of a certain quality in a certain amount of time. Both quality and production time are tied to adequate input supply and therefore inventory management. For outputs to be timely, production must be timely, and inputs must be adequate. For outputs to be of adequate quality, inputs must be in adequate supply, and of adequate quality. Both input supply and quality are contingent upon properly managed inventory and supplier relations. So, customer satisfaction in many cases is linked to proper inventory management.

Inventories are often managed by inventory management systems. Such tools and methods may be used to maintain the inventory in a desired state. The utility of inventory management systems is contingent on the inventory management systems' ability to maintain clear, accurate, and current records. Proper inventory management systems will make information about the type, location, and amount of an input or output product readily available. More advanced inventory management systems may also have analytical capabilities such as demand forecasting or is inventory optimization. Historically, there have been many different approaches to inventory management systems. There have been many different approaches because different organizations tend to have different requirements from their inventory management systems. Superior approaches to inventory management systems are often tailored to the needs of an organization. Superior approaches to inventory management systems may give organizations a significant advantage against their competitors.

Current inventory management systems often rely upon software in connection with radio-frequency identification (RFID) tags, QR readers, or barcodes. Current systems allow for a computer, smart phone, tablet, or other device to be used as part of the inventory management system. Because of the use of software and related hardware, current inventory management systems may provide automatic inventory of items as they are completely consumed, but not as they are partially depleted. Further, current systems lack a combination scale scanner device integrated into an automated system which determines amounts of partially depleted substances contained in inventory items.

The most current inventory management systems are still far from perfect. As useful as current systems are, they still have limitations. Current is systems are limited when organizations have a need to monitor the supply of a product as it is depleted. For instance, current inventory management systems may tell a user how many containers of some product are inventoried, but may not give any specific insights into whether the products have been depleted. For some organizations, like pharmaceutical, university, research, and service laboratories, the depletion of substances and remaining partial product may be a major consideration.

As alluded to above, pharmaceutical, university, research, and service laboratories often require a large inventory of reagents so that lab procedures, such as synthesis campaigns that require multi-step reactions under tight timelines, can continue without unexpected interruptions due to depleted supply of a reagent that is understocked in laboratory storage. The failure to be able to perform a mid-step in a multi-step synthesis campaign may cause the campaign to fail and threaten the laboratory's financial viability because the nature of the field requires significant investment into a single pharmaceutical or chemical product.

In another situation, the same pharmaceutical, university, research, or service laboratories may overstock reagents and accumulate waste products because partially used inventory is not tracked. Individual reagents may be slowly used over a period of months or years. Expiration is of stocked reagents is highly variable based on reagent type. Laboratory personnel tend to avoid opened and old containers, which results in expiration and waste of partially used reagent stock. Waste from unused inventory through an incomplete inventory management system that does not account for partially used substances carries significant financial and environmental costs through storage and safe disposal. Of course, there are many other economic sectors that need updated information on partially used or built-up inventory such as bars, restaurants, cosmetics. Those industries would benefit from an inventory system that tracks partially used substances by cutting the cost of storage and over-purchasing of product or material. These industries would also benefit by being able to control loss prevention of high-priced items, as well as better track demand and use of individual products or materials.

If an organization does consider partial inventory, it is piecemeal and partial supplies may only be accounted for manually at the expense of substantial time and money. Generally, partial inventory is only considered during annual or periodic physical inventory checks. These outdated methods create inventory overstocking or understocking problems that this disclosure addresses. Thus, a need exists for an inventory management system that monitors the supply of contained goods or substances as they is are gradually depleted from their containers.

LISTING OF RELATED ART

Related patent documents are incorporated in the disclosure below:

U.S. Pat. No. 6,450,406 to Brown discloses, a "Method and apparatus for inventorying substances."

U.S. Pat. No. 7,813,973 to Gudbjartsson discloses, an "Inventory monitoring system."

U.S. Pat. No. 8,229,161 to Hudnut discloses, "Vision-enabled household appliances."

U.S. Pat. No. 8,740,077 to Needham discloses, a "Medication recording device."

U.S. Pat. No. 9,002,096 to Pronkine discloses, a "Method and apparatus for determining a liquid level in a container using imaging."

U.S. Pat. No. 10,055,851 to Spector discloses, a method for "Determining dimension of target object in an image using reference object."

U.S. Pat. No. 10,332,066 to Palaniappan discloses, an "Item management system using weight."

U.S. Pat. No. 5,174,399 to Brauneis discloses, a "Point-of-sale scanner/scale system with scale activation of scanner."

U.S. Pat. No. 5,410,108 to Williams discloses, a "Combined scanner and scale."

U.S. Pat. No. 6,098,029 to Takagi discloses, a "Liquid-level position measuring method and system."

U.S. Pat. No. 7,499,581 to Tribble discloses, a "Vision system to calculate a fluid volume in a container."

U.S. Pat. No. 4,581,762 to Lapidus discloses, a "Vision inspection system."

US2019/0197466A1 to Hand discloses, "Inventory control for liquid containers."

US2020/0074402A1 to Adato discloses, "Monitoring product shortages over time."

US2006/0178578A1 to Tribble discloses, a "Vision system to calculate a fluid volume in a container."

US20180303390A1 to Hatamian discloses, a "Fluid measurement for automated medical sample collection and testing."

WO1999033008A2 to Gemmell discloses, a "System and method for collecting data on product consumption."

WO2007006309A2 to Aagaard discloses, a "Bottle weighing for an inventory control system."

KR100593098B1 to Alan discloses, an "Apparatus and method for measuring optical characteristics of an object."

JP2006138814A to Masuda discloses, a "Liquid level detection method."

EP3511036A1 to Wolfgramm discloses, an "Optical level control system."

U.S. Pat. No. 4,869,396 to Horino discloses, a "Draught beer dispensing system."

U.S. Pat. No. 5,986,219 to Carroll discloses, a "Method of inventorying liquor."

U.S. Pat. No. 6,092,726 to Toussant discloses, a "Universal monitor for collecting data on consumable products."

U.S. Pat. No. 6,601,764 to Goodwin discloses, a "System and method of managing inventory."

U.S. Pat. No. 7,458,260 to Roesner discloses, "Fluid level detection using RF."

U.S. Pat. No. 9,617,140 to Hershberger discloses, a "Draft beer supply chain systems and methods."

U.S. Pat. No. 9,727,838 to Campbell discloses, an "On-shelf tracking system."

US20050000737 to Fox discloses, a "Draughtscale for weighing draught beer."

US20050197738 to Morrison discloses, a "System and Method for Managing the Dispensation of a Bulk Product."

US20160264394 to Hershberger discloses, a "Draft beer supply chain systems and methods."

WO2005013161 to discloses, "Product inventory management."

CN101185609B to Gibson teaches, "Systems and methods for managing information relating to medical fluids and containers therefor."

JP5930961B2 to Oscar teaches, "System for managing reagent inventory."

US20170087555A1 to Morris teaches, "Methods and Systems for Using RFID in Biological Field."

SUMMARY OF THE INVENTION

In view of the foregoing, an object of this specification is to disclose a system that operates to monitor the supply of contained goods or substances.

In view of the foregoing, an object of this specification is to disclose a system that operates to monitor the supply of contained goods or substances gradually as they are depleted.

It is another object of this specification to disclose a system that operates to prevent users from ordering and opening redundant containers.

It is also an object of this specification to disclose a system that operates to monitor the supply of contained goods using software. Suitably, the system may result in optimization of inventory levels and order is amounts or frequency across a multitude of contained goods or substances. In the laboratory context, the system can optimize inventory levels and order amounts/frequencies of any multitude of reagents because reagents are susceptible to being out of stock at inconvenient times.

Yet still, it is an object of this specification to disclose a system that automatically and accurately monitors the supply of contained and partially used goods or substances.

In one embodiment, disclosed is a system for the real-time inventory of contained goods or substances. Suitably, the system may operate to monitor the supply of contained goods or substances as they are gradually depleted from their containers. Before this disclosure, monitoring the inventory of contained goods or substances was problematic in certain industries that depend on having a readily available inventory of goods or substances that may be consumed over months to years.

The system may also implement a first-in-first-out methodology. The system may reduce waste by tracking the amount of material or product stored in opened containers, as the material is depleted, by tracking how long particular containers have been stocked. Based on the information derived from tracking, users may be directed to use a partially used substance instead of a new container. Waste is reduced because a partially is used substance is prioritized over a substance from a new container.

In a preferred embodiment, the real-time inventory system has several parts. The system may include a scale scanner device that features a component that records identification data from a radio frequency identification tag (e.g., through an RFID scanner built into the scale scanner device), or alternatively a scanner component that records identification data from a QR or barcode through an embedded QR or barcode scanner. The scale scanner device may also include a built-in precision scale which may capture accurate and precise weight information from a container of material. The scale scanner device can then push the captured identification and weight information to a cloud-based inventory application. The inventory application records this data and makes it available on a client-accessible, web-based desktop or mobile device. From there, the available cloud-based data applications may be used to generate reports, create alerts, and send notices to re-stock items that are running low or anticipated to be consumed. In another application, the client may use the available data applications to generate reports and create age-based alerts to analyze or dispose of old products. In another application, the client may use the available data to automatically populate electronic laboratory notebook (ELN) tables and calculate an allowed experiment scale based on is current supply levels or required reorder amount and timeframe to perform an experiment at a desired scale.

The following may be one example of system parts:

Smart Scale

The smart scale includes a radio frequency identification reader, 1-D (Bar Code), or 2-D (QR Code) reader, and a high precision scale with load cell and amplifier components. Both components are suitably connected to an internet of things microcontroller that has Wifi Access Point and WiFi receiver. These three components work together to collect the unique ID from a scanned code, measure the gross weight from the item on the scale, and publish ID and weight to a cloud-based platform for inventory control.

Inventory Process—

The inventory process suitably begins by reading an RFID tag or scanning a 1D/2D code affixed to container housing chemical reagents, or other solid or liquid material, etc. The scale measures the weight of the scanned container. The identification of the RFID tag or 1D/2D code, scanned by RFID or scanned by QR reader or barcode, along with the gross weight of the container and contents, is pushed to the cloud-based inventory application. The inventory application correlates identification to an inventoried item and records the gross weight. The inventory application is then calculates and records net weight by subtracting the weight of the container from the gross weight measured on the scale (this is accomplished by establishing a tare weight before first use.)

Inventory Application Abilities—

The inventory application may provide supply level alerts when a weighed container is depleted and reaching zero, based on paired identification and weight information. Further, the inventory application performs supply and demand forecasting to recommend optimal levels of inventory.

The inventory application includes an online database comprised of artificial intelligence, wherein the online database stores data from a plurality of weights recorded by the precision scale in a scale scanner device or across multiple scale scanner devices. The inventory application post processes the data received from the scale scanner devices to provide analytics in a digestible format. These analytics may be used to generate use reports and show trends and forecasts through machine learning. Analytics may also be used to optimize inventory levels with size and frequency-controlled supply orders. The database allows the end user to correlate inventory with planned use, viewing items that will need to be ordered prior to their immediate need. Lead times for reorder can be added is on specified inventory items. Alerts may be based on amount needed, amount remaining, and lead time for reorder.

BRIEF DESCRIPTION OF THE SEVERAL VIEWS OF THE DRAWINGS

Other objectives of the disclosure will become apparent to those skilled in the art once the invention has been shown and described. The way these objectives and other desirable characteristics can be attained is explained in the following description and attached figures in which.

It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFERRED EMBODIMENTS

Disclosed is an inventory management system to track partial inventory of contained goods or substances. In a preferred embodiment, the real-time inventory system may include a weight scale driven by a load is cell and analog converter and amplifier, a built-in scanner device, and a contained microcontroller that records identification data from an RFID tag (e.g., through an RFID scanner built into the scale scanner device) or QR code (e.g., through a QR scanner), or barcode (e.g., through a barcode scanner). The system captures accurate and precise weight information (precision scale), by comparing the gross weight on the scale to the tared weight of the container, and pushes that information to a cloud-based inventory application. The cloud-based inventory application records this data and makes it available on a client-accessible, web-based desktop or a mobile device. Suitably, the system programmatically compares new and old data for a container to create analytics of use for particular goods or substances as they are depleted. The cloud-based platform may also direct users to use goods or substances from already opened containers. From there, the available data applications may be used to generate reports, create alerts, and send notices to re-stock items that are running low or anticipated to be consumed. Data applications may optimize inventory by alerting users to order supplies in specific sizes at specific frequencies. In another application, the client may use the available data applications to generate reports and create age-based alerts to analyze or dispose of old supplies. In another application, the client may use the available data to is automatically populate electronic laboratory notebook (ELN) tables and calculate an allowed experiment scale based on current supply levels or required reorder amount and timeframe to perform an experiment at a desired scale. The more detailed descriptions of the preferred embodiment are disclosed in connection with the attached figures.

Figure 1:
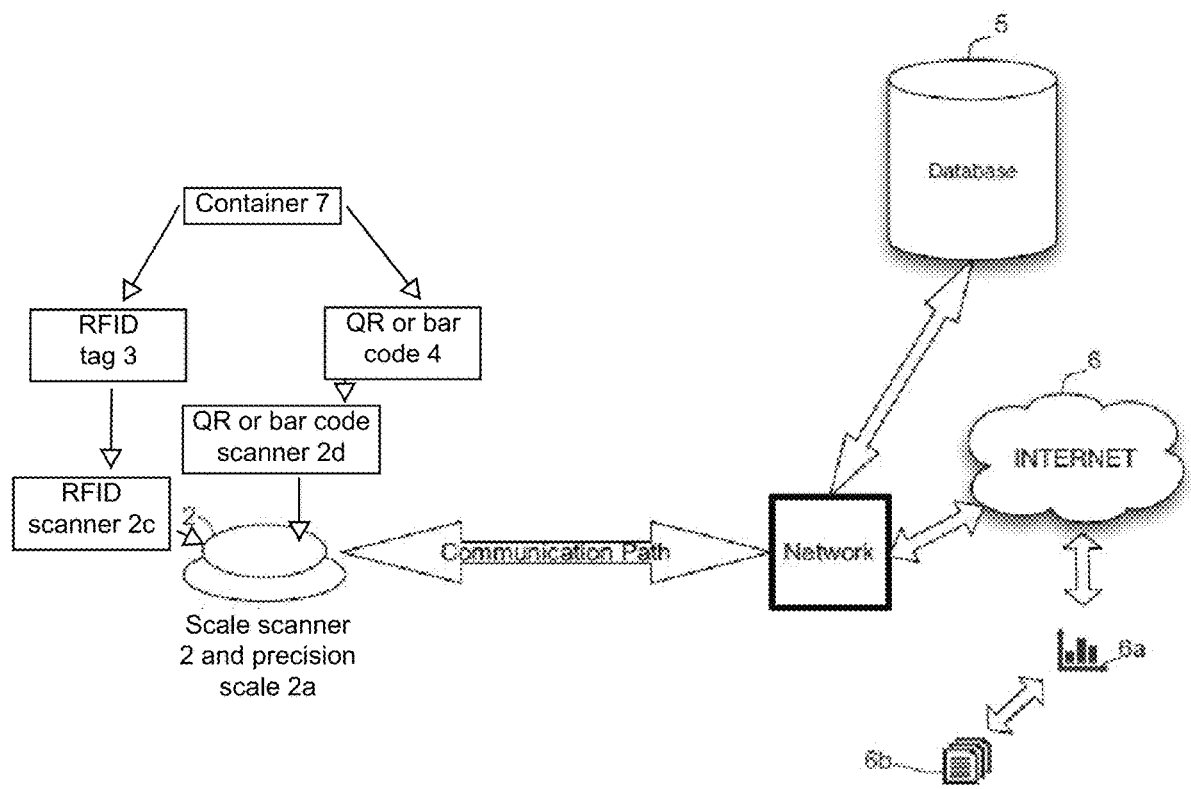
FIG. 1 is a diagram showing a plurality of hardware components of a management system for partial inventory.
Figure 2:
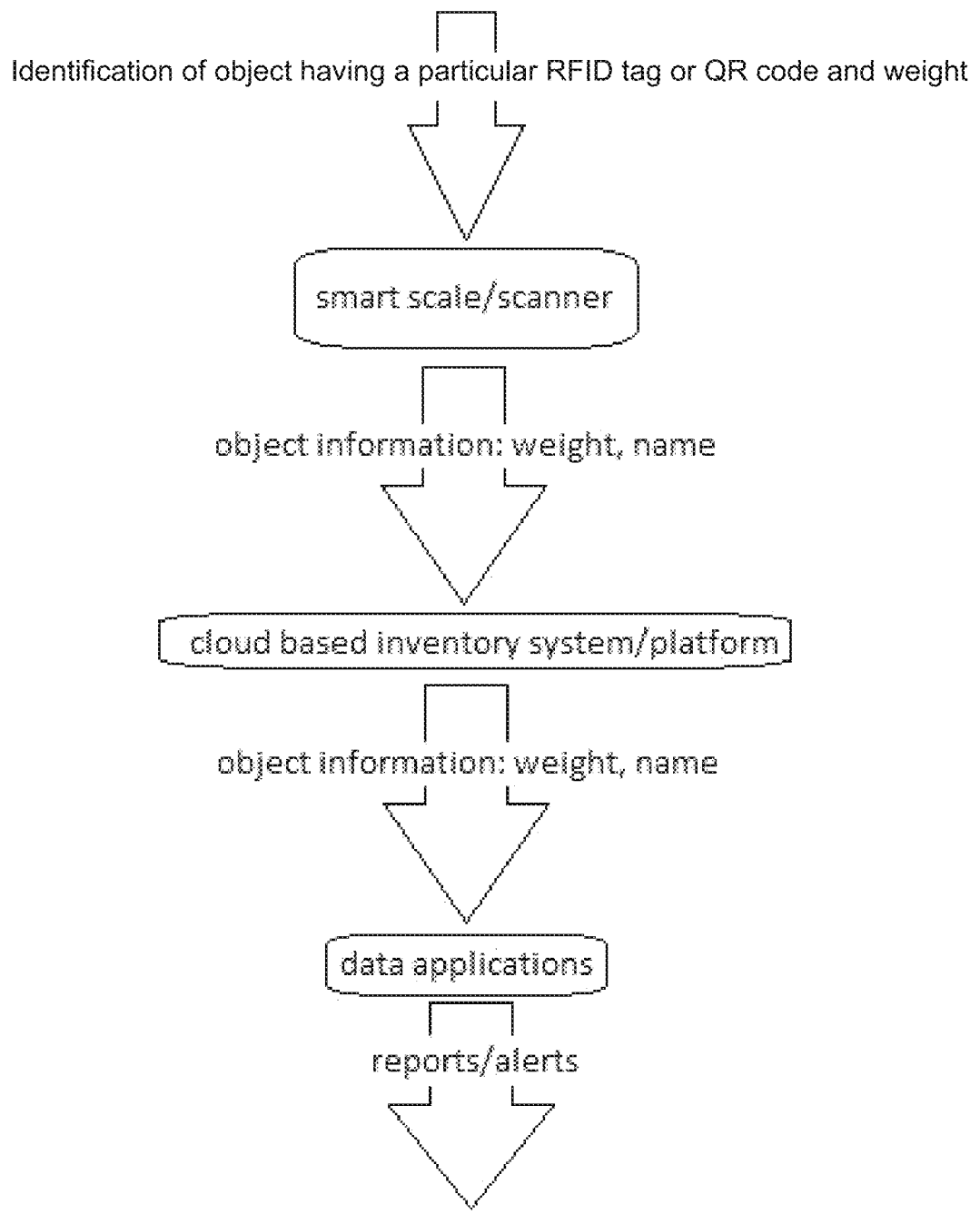
FIG. 2 is a flow chart which shows information flows from component to component of the inventory management system.

FIG. 1 is a schematic of a preferred embodiment of the disclosed system. FIG. 1 shows hardware components of the management system 1 for partial inventory. FIG. 2 depicts a flow chart that shows how and what type of information flows between components of the management system for partially consumed inventory. It should be noted that in the flow charts disclosed by this application, text superimposed on arrows represents information flow while enclosed text represents system components.

Still referring to FIGS. 1 and 2, in a preferred embodiment, the management system 1 for partial inventory has several components. The system has a scale scanner device 2 that records identification data from an RFID tag 3 of a container 7 (through an RFID scanner 2c), accurate and precise weight information (through a precision scale 2a) from the container 7, and pushes that information to a cloud-based inventory platform 5. In the alternative embodiment, the data recorder may be either a QR scanner or is barcode scanner 2d that reads a QR or bar code 4 on the container 7. The cloud-based inventory application 5 records this data and makes it available on a client-accessible, web-based desktop or mobile device 6. A client may use a plurality of available data to create alerts 6a to re-stock items that are running low or anticipated to be consumed, or to create reports 6b to optimize inventories. In another application, the client may use the available data to create age-based alerts 6a to analyze and dispose of old products.

FIG. 3a through 3d show two different embodiments of the smart scale scanner device 2.

Figure 3A:
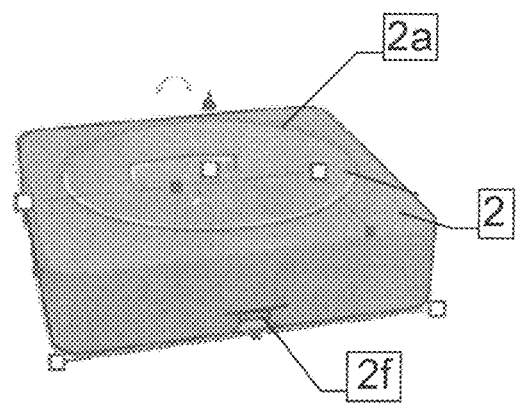
FIG. 3a is a perspective view of a preferred embodiment of a scale scanner device.
Figure 3B:
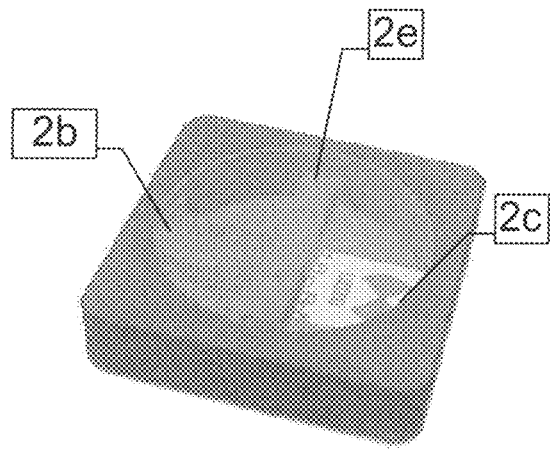
FIG. 3b is a top view of the preferred embodiment of the scale scanner device.

The preferred embodiment shown in FIGS. 3a and 3b is a square-shaped scale scanner device 2, and as shown features a surface that functions as a precision scale 2a. The surface of the precision scale 2a may be glass, plexiglass, metal, or plastic or metal composite. A microcontroller 2b, with Wifi and Wifi Direct capabilities, controls device components and records and transmits identification and weight information. A feature of the device is the RFID scanner 2c. Another shown component is a load cell 2e. The load cell 2e may be a type of force transducer which converts the weight of the container 7 into an electrical signal that can be measured. The scale scanner device 2 is powered by a USB port 2f. Because the preferred embodiment scale scanner 2 does not scan barcodes or QR codes it does not feature a QR camera or barcode scanner 2d.

Figure 3C:
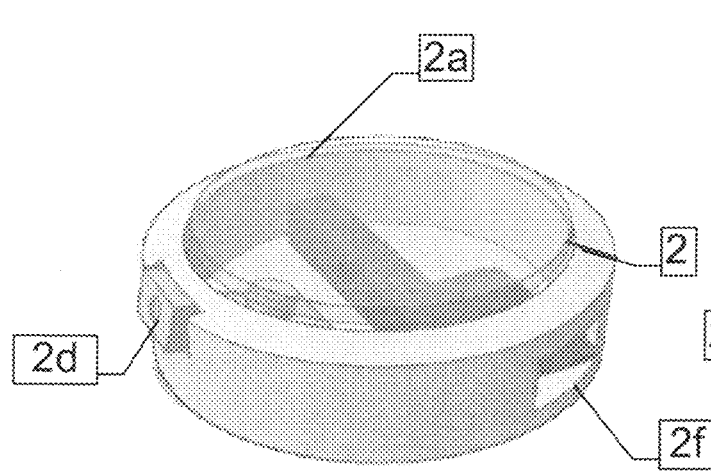
FIG. 3c is a perspective view of an alternative embodiment of the scale scanner device.
Figure 3D:
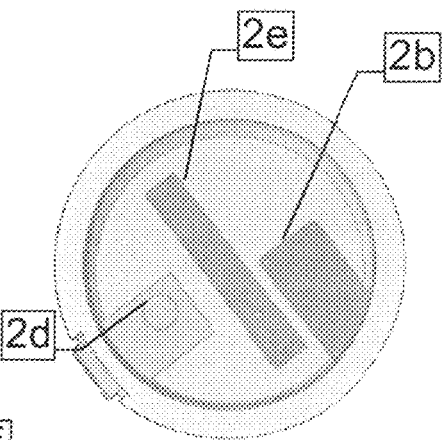
FIG. 3d is a perspective view of the alternative embodiment of the scale scanner device.

An alternative embodiment is shown by FIGS. 3c and 3d. The alternative embodiment shown in FIGS. 3c and 3d shares some similarities with, yet is in some ways different from, the preferred embodiment shown in FIGS. 3a and 3b. The alternative embodiment is circular and features a QR camera or barcode reader 2d. Aside from differences related to cameras and identification mechanisms, both embodiments share common features such as the precision scale 2a, microcontroller 2b, load cell 2e, and USB port 2f.

Figure 4:
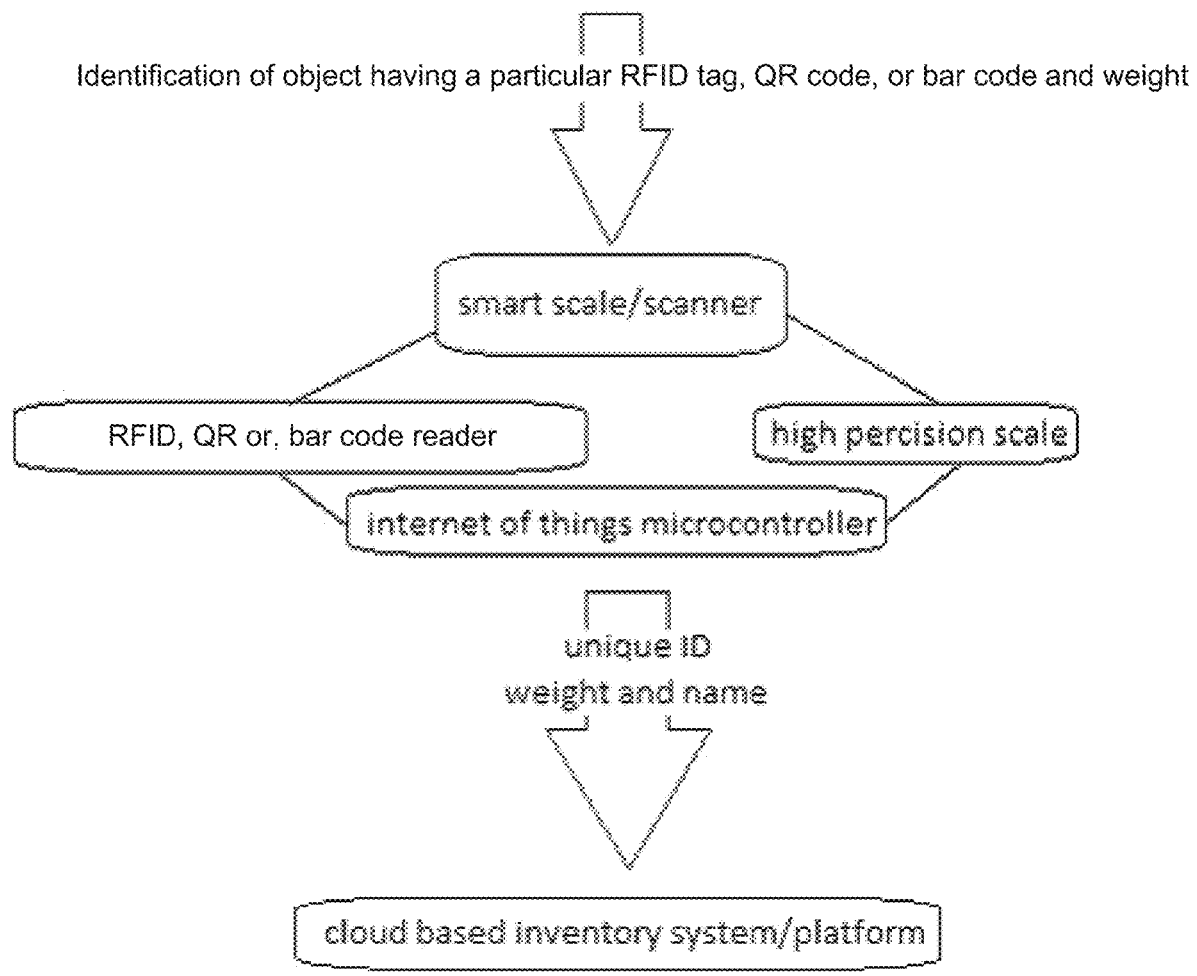
FIG. 4 is a flow chart which shows information flow through the smart scale scanner device.

FIG. 4 shows a flow chart which demonstrates how the smart scale scanner device 2 uses its subsystems to create object information to be sent to the inventory management platform 5. The smart scale scanner device 2 may include an RFID scanner 2c or QR or bar code reader 2d, and a high precision scale 2a. In a preferred embodiment, there may be an RFID scanner 2c to receive data from an RFID tag 3 placed on a container 7. These components may be integrated. Both components may be connected to an internet of things microcontroller 2b. The RFID scanner 2c, scale 2a, load cell 2e, and microcontroller 2b work together to collect a is unique ID containing specific information from the RFID tag 3 or alternatively the QR or barcode 4 to measure the gross weight from the container 7 on the scale 2a, and publish ID and weight information to the cloud-based inventory platform 5.

Figure 5:
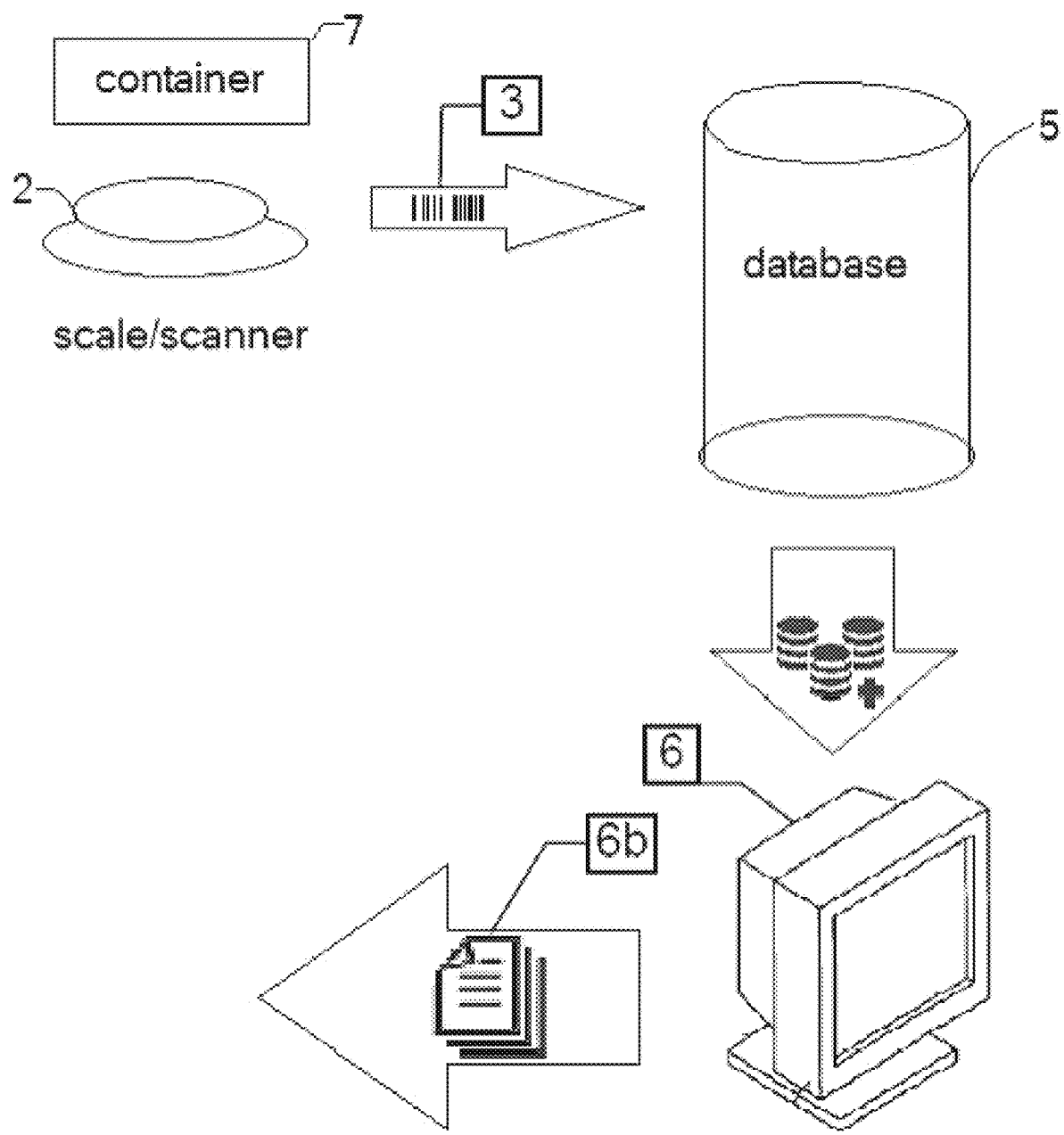
FIG. 5 is a diagram that shows information flow and processing through the inventory management system.

FIG. 5 is a diagram that shows information flow and processing through the inventory management system 1. FIG. 5 speaks to an inventory process and the inventory platform 5 capabilities. The inventory process may begin with the RFID reader 2c, or QR/barcode scanner 2d, reading or scanning an RFID tag 3 or 1D/2D QR code or barcode 4 affixed to a container 7 housing some substance, for instance chemical reagents, solid or liquid materials, etc. The scale 2a may then measure the weight of the scanned container 7. The identification of the RFID tag 3 or 1D/2D QR code or barcode 4 read or scanned by the RFID scanner 2c or QR or barcode scanner 2d, along with the gross weight of the container 7 and contents, may be pushed to the cloud-based inventory platform 5. The inventory platform 5 may correlate identification to an inventoried item and record the gross weight. The inventory platform 5 may then calculate and record net weight by subtracting the weight of the container 7 from gross weight on the scale 2a (this is accomplished by establishing a tare weight before first use.) Thereafter the user, via the web-based desktop or mobile is device 6 and cloud-based platform 5, may analyze available data and produce supply level alerts 6a and reports 6b containing supply and demand forecasts. The cloud-based platform 5 may also automatically populate electronic laboratory notebook (ELN) tables and calculate an allowed experiment scale based on current supply levels or required reorder amount and timeframe to perform an experiment at a desired scale.

Figure 6:
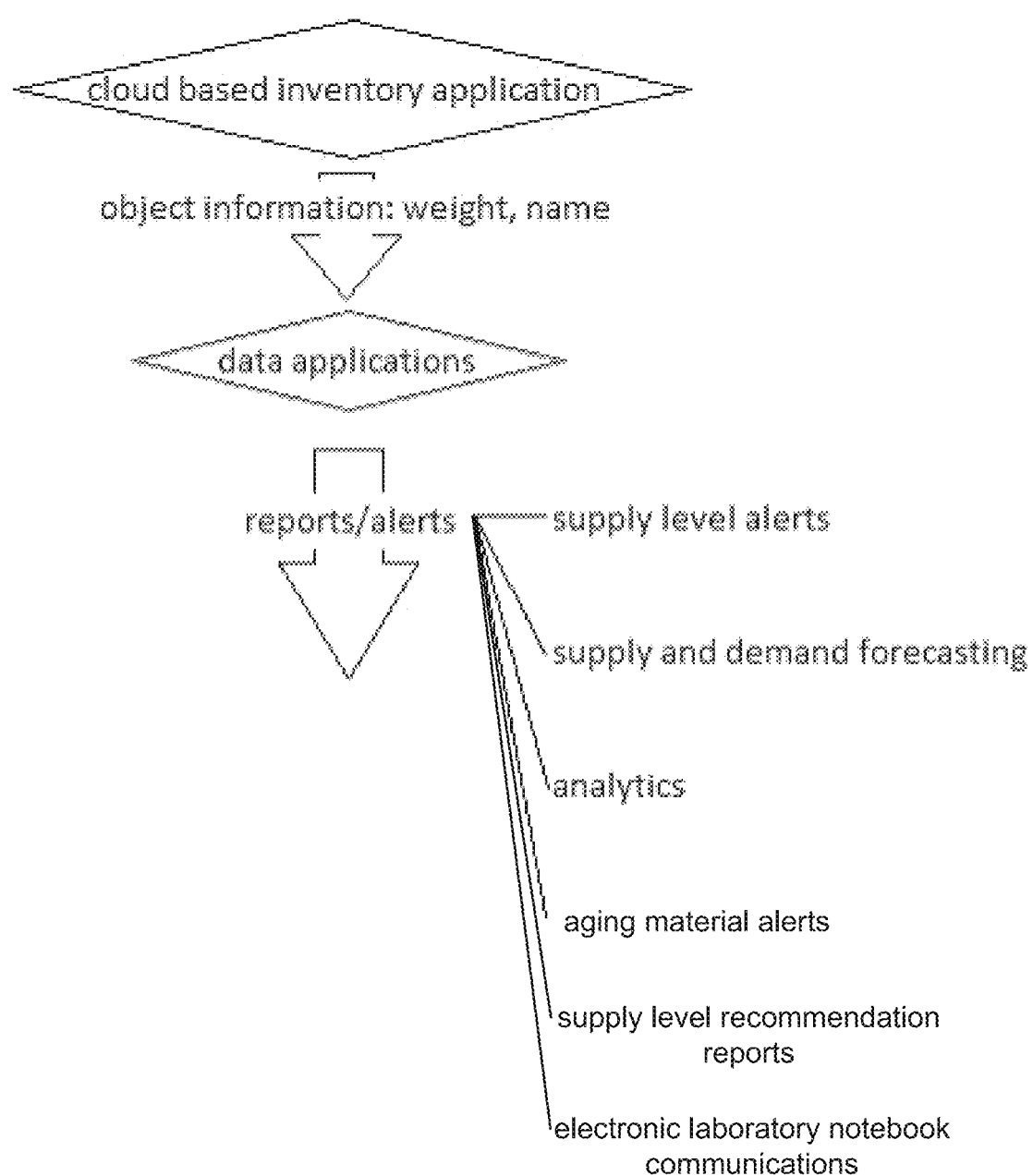
FIG. 6 is a flow chart which displays information flow through the inventory application/platform.

FIG. 6 shows a flow chart illustrating how information moves through the web-based desktop or mobile device 6 and cloud-based platform 5 to create deliverables such as alerts 6a and reports 6b. The web-based desktop or mobile device 6 and cloud-based platform 5 may provide supply level alerts 6a when a weighed container 7 is about to be empty based on paired identification and weight information. Alerts 6a may also include aging material alerts for analysis or disposal of old substances. Further, the cloud-based platform 5 may perform supply and demand forecasting driven by machine learning, and generate reports 6b to recommend optimal levels of inventory.

The inventory platform 5 includes an online database comprised of artificial intelligence, wherein the online database stores data from a plurality of weights recorded by smart scale scanners 2 and paired in the cloud 5. The cloud-based platform 5 may process data received from the is smart scale scanner devices 2 to provide analytics in a digestible format. These analytics may be used to generate reports 6b and show trends and forecasts through machine learning. The end user may correlate inventory with planned use, including data communications between database 5 and an electronic laboratory notebook, allowing for viewing of items that will need to be ordered prior to their immediate need. Lead times for reorder can be added on specified inventory items. Alerts 6a may be based on amount needed, amount remaining, and lead time for reorder.

Figure 7:
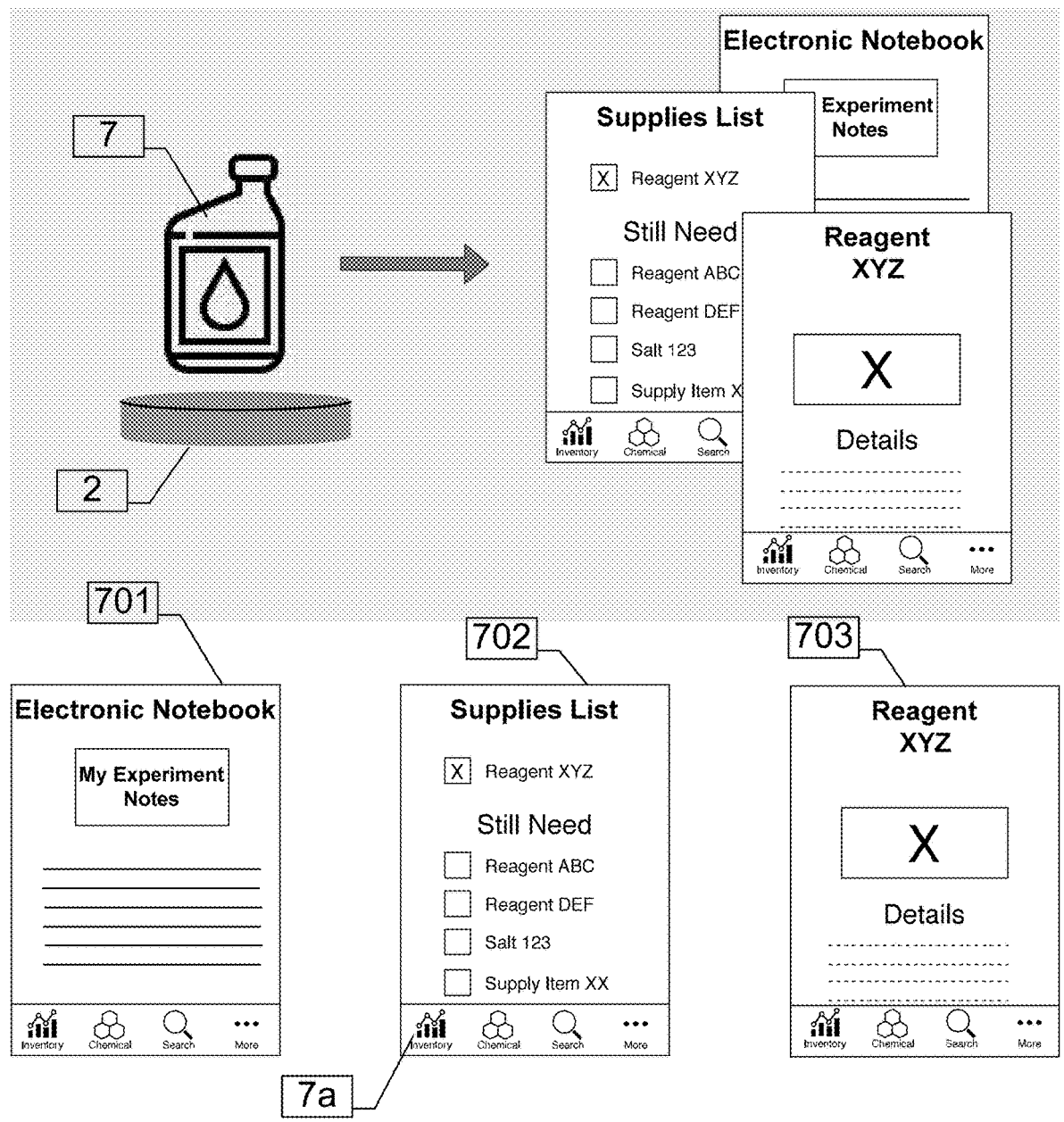
FIG. 7 contains views of a user interface for supply level for an experiment or planned use; and, FIG. 8 contains views of a user interface for returned reagent and material supply status.

FIG. 7 speaks to the user interfaces associated with forecasting, analytics and electronic laboratory notebook population when scanning a container 7. As shown, a container 7, is checked back into inventory after use. When the container 7 is scanned, a plurality of pages may populate the user interface. Pages that may populate a device 6 screen are an electronic laboratory notebook 701, a supplies list 702, and an item detail page 703. Each page has a different purpose; however, all pages may feature a navigation table 7a at the bottom of the page.

The electronic laboratory notebook 701 may be automatically populated from the database of the cloud-based platform 5. Calculations related to an allowed experiment scale based on current supply levels or required reorder amount and timeframe to perform an experiment at a is desired scale may be stored in the electronic laboratory notebook 701.

The supplies list page 702 may indicate to the user what supplies are properly stocked and what supplies need to be ordered. The supplies list may be a check mark list or any other type of list. Supply lists may be organized by urgency, amount needed, time in storage, alphabetically, and the like.

The item detail page 703 may include specific qualified or quantified information about a specific contained substance.

Figure 8:
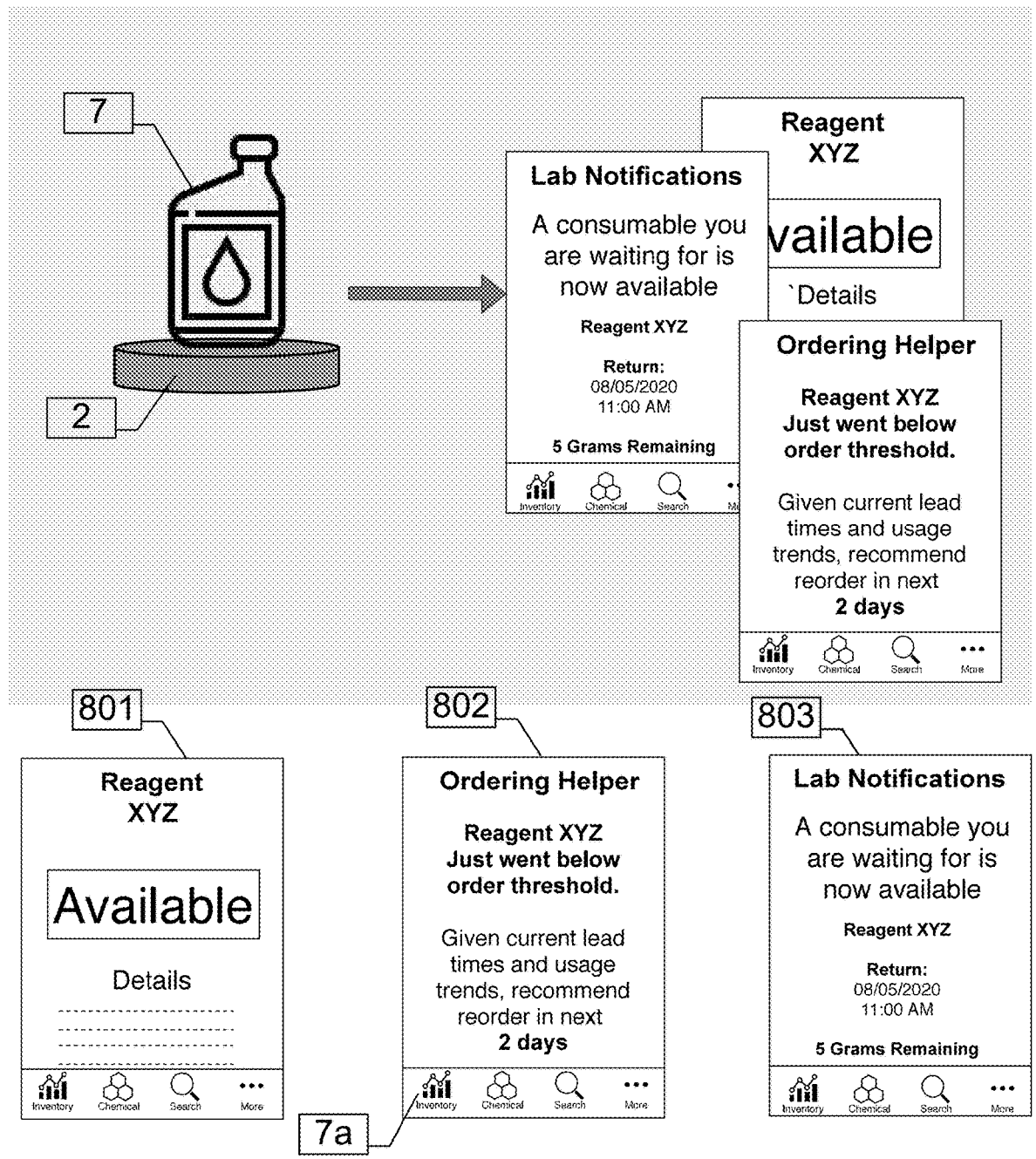

FIG. 8 speaks to the featured alerts generated when returning a used container 7. Pages that may populate a device 6 screen may be the availability of a reagent or item 801, an ordering helper page 802, or a lab notification page 803. Pages may feature a navigation table 7a at the bottom of the page.

The availability page 801 alerts users to the availability of a particular item that has been returned to inventory.

The ordering helper page 802 seeks to help users maintain adequate supplies of different contained substances. The ordering helper page 802 may indicate to a user that a contained substance is dropping below a predefined threshold. If it is the case that the substance is below the threshold, the ordering helper page 802 may prompt the user to order more is of substance which is in inadequate supply. The ordering helper page 802 may consider analytics and data such as lead times and usage trends when prompting the user to order a substance.

The lab notifications page 803 may indicate to the user that a substance is now available. The lab notifications page 803 may disclose information related to when a substance was returned and how much substance remained in the container 7 when the container 7 was returned.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus, the breadth and scope of the claimed invention should not be limited by any of the above-described embodiments.

Terms and phrases used in this document, and variations thereof, is unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality is described or claimed as part of the module are all configured in a common package. Indeed, any or all the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

All original claims submitted with this specification are incorporated by reference in their entirety as if fully set forth herein.

PAPER "SEQUENCE LISTING"

Not applicable.

We claim:

1. An inventory management system capable of tracking and accounting for a partially used inventory comprising:
a scale scanner device to determine a weight of a container including a weight of a particular supply by determining a difference between a gross weight of the container and a net weight of the container and obtain a unique identifier by scanning at least one of a radio frequency identification (RFID) tag, a one-dimensional code, and a two-dimensional code associated with the container; and
at least one computing device to:
transmit the weight of the particular supply and the unique identifier;
determine a reorder amount and a reorder time for the particular supply for planned use to perform an experiment at a desired experiment scale based on an amount of the particular supply needed, an amount of the particular supply remaining, an age of the particular supply remaining to determine when the particular supply is expired, a number of steps in the experiment, a particular step number of the number of steps in the experiment for the particular supply, a lead time for reorder, and analytics from a plurality of scale scanner devices, the analytics based on machine learning information from the plurality of scale scanner devices and past experiments associated with the plurality of scale scanner devices;
generate a first graphical user interface (GUI) that indicates the weight of the container and the unique identifier in an electronic laboratory notebook, a second GUI that indicates a supplies list, a third GUI that indicates item detail information, and a navigation table that is always displayed at a bottom of a display screen, the first GUI displayed, the second GUI hidden, and the third GUI hidden when a first navigation button of the navigation table is selected, the first GUI hidden, the second GUI displayed, and the third GUI hidden when a second navigation button of the navigation table is selected, and the first GUI hidden, the second GUI hidden, and the third GUI displayed when a third navigation button of the navigation table is selected.

2. The inventory management system of claim 1 wherein the scale scanner device comprises a radio frequency identification (RFID) scanner.

3. The inventory management system of claim 1 wherein the scale scanner comprises a QR or bar code scanner.

4. The inventory management system of claim 2 the at least one processor further to transmit a cloud-based inventory platform.

5. The inventory management system of claim 4 wherein the scale scanner device comprises a data connection to the cloud-based inventory platform.

6. The inventory management system of claim 5 wherein the cloud-based inventory platform automatically populates the electronic laboratory notebook in a plurality of electronic laboratory notebook tables with supply metrics.

7. The inventory management system of claim 6 further comprising data processing firmware.

8. A management system for partial inventory comprising:
a scale scanner device to determine a weight of a container including a weight of a particular supply by determining a difference between a gross weight of the container and a net weight of the container; and
obtain a unique identifier by scanning at least one of a radio frequency identification (RFID) tag, a one-dimensional code, and a two-dimensional code associated with the container; and
at least one computing device to provide a cloud-based inventory platform to:
transmit the weight of the particular supply and the unique identifier;
determine a reorder amount and a reorder time for the particular supply for planned use to perform an experiment at a desired experiment scale based on an amount of the particular supply needed, an amount of the particular supply remaining, an age of the particular supply remaining to determine when the particular supply is expired, a number of steps in the experiment, a particular step number of the number of steps in the experiment for the particular supply, a lead time for reorder, and analytics from a plurality of scale scanner devices, the analytics based on machine learning information from the plurality of scale scanner devices and past experiments associated with the plurality of scale scanner devices; and
generate a first graphical user interface (GUI) that indicates the weight of the container and the unique identifier in an electronic laboratory notebook, a second GUI that indicates a supplies list, a third GUI that indicates item detail information, and a navigation table that is always displayed at a bottom of a display screen, the first GUI displayed, the second GUI hidden, and the third GUI hidden when a first navigation button of the navigation table is selected, the first GUI hidden, the second GUI displayed, and the third GUI hidden when a second navigation button of the navigation table is selected, and the first GUI hidden, the second GUI hidden, and the third GUI displayed when a third navigation button of the navigation table is selected.

9. The inventory management system of claim 8 wherein the scale scanner device and the at least one computing device share data connectivity.

10. The inventory management system of claim 8 wherein the scale scanner device comprises an integrated scale and scanner.

11. The inventory management system of claim 10 wherein the integrated scale and scanner comprises at least one of glass, plexiglass, metal, plastic, and metal or plastic composite.

12. The inventory management system of claim 11 wherein the scale scanner device comprises an internet of things microcontroller.

13. The inventory management system of claim 12 further comprising a database storing net weight information for inventoried items.

14. A method of managing inventory comprising:
- scanning, by a scanner scale device, a radio frequency identification (RFID) tag, QR code, or barcode of a partially filled container;
- determining, by the scanner scale device, a weight of the container including a weight of a particular supply by determining a difference between a gross weight of the container and a net weight of the container;
- transmitting by the scanner scale device RFID, QR, bar code, and weight information to at least one computing device;
- determining, by the at least one computing device, a reorder amount and a reorder time for the particular supply for planned use to perform an experiment at a desired experiment scale based on an amount of the particular supply needed, an amount of the particular supply remaining, an age of the particular supply remaining to determine when the particular supply is expired, a number of steps in the experiment, a particular step number of the number of steps in the experiment for the particular supply, a lead time for reorder, and analytics from a plurality of scale scanner devices, the analytics based on machine learning information from the plurality of scale scanner devices and past experiments associated with the plurality of scale scanner devices; and
- generating, by the at least one computing device, a first graphical user interface (GUI) that indicates the weight of the container and a unique identifier for the particular supply in the container in an electronic laboratory notebook, a second GUI that indicates a supplies list, a third GUI that indicates item detail information, and a navigation table that is always displayed at a bottom of a display screen, the first GUI displayed, the second GUI hidden, and the third GUI hidden when a first navigation button of the navigation table is selected, the first GUI hidden, the second GUI displayed, and the third GUI hidden when a second navigation button of the navigation table is selected, and the first GUI hidden, the second GUI hidden, and the third GUI displayed when a third navigation button of the navigation table is selected.

15. The method of claim 14 further comprising analyzing data by the at least one computing device.

16. The method of claim 15 further comprising updating, by the at least one computing device, a database with an amount remaining in a container.

17. The method of claim 16 further comprising generating, by the at least one computing device, a supply level alert.

18. The method of claim 17 further comprising producing, by the at least one computing device, a supply optimization report.

19. The method of claim 18 further comprising producing, by the at least one computing device, a supply and demand forecast.

20. The method of claim 19 further comprising generating, by the at least one computing device, an ordering helper graphical user interface (GUI) prompting a user to order more containers of items that are in inadequate supply.

* * * * *